(12) United States Patent
Konrad et al.

(10) Patent No.: US 6,719,811 B1
(45) Date of Patent: Apr. 13, 2004

(54) OXIDATION COLORANTS FOR KERATIN FIBERS

(75) Inventors: Guenther Konrad, Hilden (DE); Iduna Matzik, Essen (DE); Edgar Lieske, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 1,964 days.

(21) Appl. No.: 07/949,851

(22) PCT Filed: May 10, 1991

(86) PCT No.: PCT/EP91/00874
§ 371 (c)(1),
(2), (4) Date: Nov. 19, 1992

(87) PCT Pub. No.: WO91/17739
PCT Pub. Date: Nov. 28, 1991

(30) Foreign Application Priority Data

May 19, 1990 (DE) .......................................... 40 16 177

(51) Int. Cl.$^7$ ................................................ A61K 7/13
(52) U.S. Cl. ...................... 8/409; 8/405; 8/406; 8/408; 8/410; 8/416; 8/421; 8/423
(58) Field of Search ............................ 8/406, 408, 405, 8/407, 409, 410, 416, 421, 423; 552/302; 548/508

(56) References Cited

U.S. PATENT DOCUMENTS

| | | | | |
|---|---|---|---|---|
| 2,934,396 A | * | 4/1960 | Charle et al. ..................... | 8/11 |
| 3,194,734 A | * | 7/1965 | Seemuller et al. ............. | 8/406 |
| 4,013,404 A | * | 3/1977 | Parent ......................... | 8/423 |
| 5,011,500 A | * | 4/1991 | Grollier et al. ................ | 8/410 |
| 5,021,067 A | * | 6/1991 | Grollier ......................... | 8/409 |
| 5,178,637 A | * | 1/1993 | Lagrange et al. ............. | 8/405 |

FOREIGN PATENT DOCUMENTS

| DE | 1916139 | 11/1969 |
|---|---|---|
| GB | 2033392 | 5/1980 |

OTHER PUBLICATIONS

Journal of Chemical Society (C), vol. 15, 1970, (Newcastle upon Tyne, GB), F. Binns, et al.: "Studies Related to The Chemistry Of Melanins. Part XIII. Studies On the Structure Of Dopamine–Melanin", pp. 2063–2070.

Journal of Chemical Society (C), 1967, (Newcastle upon Tyne), S.N. Mishra, et al.: "Studies Related To The Chemistry Of Melanins. Part III. Synthesis Of 5,6–Dihydroxyindoline", pp. 1424–1427.

Journal of Medicinal Chemistry, vol. 21, No. 6, 1978, (University of California, San Francisco, California), C. G. Chavdarian, et al.: "Oxidative And Cardiovascular Studies On Natural And Synthetic Catecholamines", pp. 548–554.

* cited by examiner

*Primary Examiner*—Margaret Einsmann
(74) *Attorney, Agent, or Firm*—Stephen D. Harper; Glenn E. J. Murphy

(57) ABSTRACT

The use of indolines of formula (I):

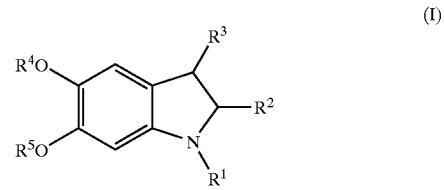

in which $R^1$, $R^2$, $R^3$, $R^4$ and $R^5$ independently of one another represent hydrogen or $C_{1-4}$ alkyl groups, or $R^4$ and $R^5$ together with the oxygen atoms to which they are attached may represent an alkylenedioxy group containing 1 to 4 carbon atoms, or their salts, as oxidation dye precursors gives natural brown hair colorings. The indolines of formula (I) are also suitable as couplers in oxidation hair dyes with a conventional primary intermediate, in which they result in a modification of the tints obtainable with the primary intermediate. They are used in conventional carriers, e.g., in gel or emulsion form, preferably mixed before use or on the hair with an oxidizing agent to develop the color.

14 Claims, No Drawings

OXIDATION COLORANTS FOR KERATIN FIBERS

FIELD OF THE INVENTION

This invention relates to the use of indoline derivatives, more particularly 5,6-dihydroxyindolines, as an oxidation dye precursor for the production of oxidative dyeing compositions for keratin fibers, more particularly for human hair.

STATEMENT OF RELATED ART

Natural hair dyes, so-called melanins, are formed during their biosynthesis by the oxidative polymerization of 5,6-dihydroxyindole. Accordingly, numerous attempts have been made in the past to use 5,6-dihydroxyindole as a reactive dye precursor in the dyeing of hair. Unfortunately, 5,6-dihydroxyindole is extremely unstable both in free form and in the form of its salts in aqueous solution and, in the presence of atmospheric oxygen, very quickly forms insoluble, colored oxidation and polymerization products which can no longer be fixed to the hair. Accordingly, all attempts to use 5,6-dihydroxyindole itself or its salts in dye preparations have led to unsatisfactory and commercially unusable hair dyes.

DESCRIPTION OF THE INVENTION

A new and surprising possibility has now been found for producing natural hair colors with melanin dyes via a 5,6-dihydroxyindole formed "in situ" without any of the stability problems typical of 5,6-dihydroxyindole.

SUMMARY OF THE INVENTION

The present invention relates to the use of indolines corresponding to formula I:

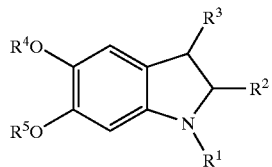

(I)

in which $R^1$, $R^2$, $R^3$, $R^4$, and $R^5$ independently of one another represent hydrogen or $C_{1-4}$ alkyl groups; or $R^4$ and $R^5$ together with the oxygen atoms to which they are attached may represent an alkylenedioxy group containing 1 to 4 carbon atoms, or salts thereof as oxidation dye precursors for the generation of oxidative dyeings.

DESCRIPTION OF PREFERRED EMBODIMENTS 5,6-Dihydroxyindoline, i.e. the indoline derivative corresponding to formula I, when $R^1$, $R^2$, $R^3$, $R^4$, and $R^5$ are hydrogen, is particularly suitable because it forms 5,6-dihydroxyindole and also melanin dye during the oxidation. However, it is also known that derivatives of 5,6-dihydroxyindole form dyes similar to melanin under oxidation conditions. Accordingly, the alkyl-substituted indolines corresponding to formula I, preferably those in which one of the groups $R^1$, $R^2$ and $R^3$ is a methyl group and the others are hydrogen, are suitable for use as oxidation dye precursors for the production of storable dye preparations.

By virtue of the chemical similarity of the melanin dyes formed from the indolines to be used in accordance with the invention to the natural melanin dye, the dye preparations produced therewith can be expected to show favorable toxicological and dermatological behavior. Above all, however, particularly natural color tones in the mid-blond to mid-brown range with high fastness to light, mechanical friction, chemical treatment, for example with reducing cold-wave preparations, and to washing with surfactant solutions are obtained.

5,6-Dimethoxyindoline and 5,6-dihydroxyindoline are known from the literature, their production being described, for example, in *J. Chem. Soc.* (C), 1967, pages 1424 to 1427. The alkyl-substituted indolines corresponding to formula I can be similarly prepared from the correspondingly substituted 5,6-dihydroxyindoles or alkoxyindoles by catalytic hydrogenation. Another process for the production of 5,6-dihydroxyindolines from 5,6-dimethoxyindoles by reduction with sodium cyanoborohydride and elimination of the methoxy groups in concentrated hydrochloric acid is described in *Journal of Medicinal Chemistry*, 1978, Vol. 21, No. 6, page 553.

The indolines of formula I to be used in accordance with the invention are preferably used as sole oxidation dye precursors. They may be used in free form or in the form of their salts, preferably as hydrochlorides, hydrobromides, sulfates, phosphates, acetates, propionates, lactates or citrates.

However, other known oxidation dye precursors and, optionally, known substantive dyes may also be used together with the indolines corresponding to formula I for modifying the color tones.

In particular, it has been found that the indolines corresponding to formula I and also their salts are also eminently suitable for use as color modifiers in oxidation hair dyes containing typical primary intermediate compounds.

Accordingly, the present invention also relates to hair dyes containing oxidation dye precursors in a carrier, characterized in that they contain indolines corresponding to formula I or salts thereof as color modifiers together with the primary intermediate compounds typically used for oxidation hair dyes. The indolines corresponding to formula I modify the colors obtainable with the primary intermediate compounds alone by self-coupling and lead to intensive, brilliant dark-brown to blue-black tones.

The hair dyes according to the invention preferably contain a mildly basic carrier.

The typical primary intermediate components used may be any of the compounds known for this purpose. Those of the aromatic or heterocyclic amino compound type are preferred. Suitable primary intermediate compounds of this type are, for example, p-phenylenediamine, p-tolylenediamine, 2-chloro-p-phenylenediamine, N-methyl-p-phenylenediamine, N,N-diethyl-p-phenylenediamine, N-(β-hydroxyethyl)-p-phenylenediamine, N,N-dimethyl-p-phenylenediamine, N,N-bis-(β-hydroxyethyl)-p-phenylenediamine, 2,5-diaminobenzyl alcohol and other compounds of the type mentioned which may also contain one or more $NH_2$ groups, NHR groups, or $NR_2$ groups, in which R represents $C_{1-4}$ alkyl groups or $C_{2-4}$ hydroxyalkyl groups, and also p-aminophenols, 1-amino-4-naphthol or tetraaminopyrimidines, for example 2,4,5,6-tetraaminopyrimidine or 2-dimethylamino-4,5,6-triaminopyrimidine, diaminopyrimidines, or 1-phenyl-3-carboxamido-4-amino-5-pyrazolone.

Where the indolines corresponding to formula I are used as color modifiers for modifying the color tone of the primary intermediate compounds mentioned, they are used in quantities of 0.1 to 10 millimole per 100 g of the hair dye. They are typically used in substantially molar quantities, based on the primary intermediate compounds used.

Although it has proved to be advisable to use molar quantities, there is no disadvantage in using an excess of individual oxidation dye precursors.

The indolines corresponding to formula I do not have to be individual chemical compounds, instead they may also be mixtures of the indolines, corresponding to formula I or their salts to be used in accordance with the invention.

To produce oxidative dyeing compositions, the oxidation dye precursors are incorporated in a suitable carrier. Such carriers are, for example, creams, emulsions, gels, or even surfactant-containing foaming solutions (shampoos), foam aerosols, or other preparations suitable for application to the hair. The carriers in question contain formulation and dyeing aids which increase the stability of the preparations and improve the result of dyeing. Such additives are, primarily, surface-active agents, for example

- soaps, more particularly the alkali metal or alkanolamine soaps of linear $C_{12-18}$ fatty acids, more particularly oleic acid,
- anionic surfactants, for example fatty alcohol sulfates and fatty alcohol polyglycol ether sulfates, alkane sulfonates, α-olefin sulfonates, or oleic acid sulfonates, preferably in the form of their alkali metal, ammonium, or alkanolammonium salts
- cationic surfactants, for example alkyl ($C_{12-18}$) trimethyl ammonium chloride, alkyl ($C_{12-18}$) dimethyl benzyl ammonium salts, cetyl pyridinium chloride, 2-hydroxydodecyl hydroxyethyl dimethyl ammonium chloride
- zwitterionic surfactants such as, for example, alkyl ($C_{12-18}$) dimethyl ammonium glycinate, coconut oil acylaminopropyl dimethyl ammonium glycinate or imidazolinium betaines
- amphoteric surfactants such as, for example, N-dodecylaminoacetic acid, N-cetylaminopropionic acid, Y-laurylaminobutyric acid and
- nonionic surfactants, more particularly adducts of 5 to 30 mol ethylene oxide with fatty alcohols, with alkylphenols, with fatty acids, with fatty acid alkanolamides, with fatty acid partial glycerides, with fatty acid sorbitan partial esters, or with fatty acid methyl glucoside partial esters, also alkyl glucosides, amine oxides, and fatty acid polyglycerol esters. Other formulation aids are
- water-soluble thickening polymers (hydrocolloids), for example cellulose ethers, such as carboxymethyl cellulose, hydroxyethyl cellulose, methyl cellulose, methyl hydroxypropyl cellulose, starch and starch ethers, vegetable gums, guar gum, agar agar, alginates, xanthan gum, or synthetic water-soluble polymers
- antioxidants, for example ascorbic acid, $Na_2SO_3$,
- buffers, for example ammonium chloride and ammonium sulfates
- complexing agents, for example 1-hydroxyethane-1,1-diphosphonic acid, nitrilotriacetic acid or ethylenediamine tetraacetic acid or salts thereof,
- hair-cosmetic auxiliaries, for example water-soluble cationic polymers, protein derivatives, glucose, D-panthenol, cholesterol, vitamins or vegetable extracts,
- levelling aids, for example urazole, hexahydropyrimidin-2-one, imidazole, 1,2,4-triazole, or iodides, for example sodium or potassium iodide.

The hair dyes according to the invention may be applied in the mildly acidic, neutral, or mildly alkaline pH range.

One preferred embodiment of the invention are hair dyes with a content of oxidation dye precursors in a carrier which contain indolines corresponding to formula I or salts thereof in a quantity of 0.1 to 20 millimole per 100 g of hair dye as oxidation dye precursors and, as carrier, a gel containing 1 to 20% by weight of a soap or an oil-in-water emulsion containing 1 to 25% by weight of a fatty component and 0.5 to 30% by weight of an emulsifier from the group of anionic, nonionic, cationic, zwitterionic, or ampholytic surfactants.

Preferred neutral or mildly acidic carriers for the dye preparation are oil-in-water cream emulsions containing $C_{12-22}$ fatty alcohols, preferably cetyl and stearyl alcohol, as fatty component and nonionic, zwitterionic, or cationic emulsifiers, preferably adducts of 10 to 30 moles of ethylene oxide with cetyl and stearyl alcohol, which may optionally be adjusted to a pH value of 2.5 to 4 by addition of citric acid or other weak acids.

The indoline of formula I to be used in accordance with the invention is incorporated in this emulsion in a quantity of 2 to 20 millimoles per 100 g.

Preferred mildly basic carriers for the dye preparation are gels or oil-in-water emulsions. Suitable gels contain 1 to 20% by weight of a soap, preferably ammonium oleate, and preferably 1 to 10% by weight of a nonionic emulsifier as surface-active agents and 5 to 20% by weight of a $C_{12-22}$ fatty alcohol as fatty component. Suitable oil-in-water emulsions contain 1 to 25% by weight of a fatty component, preferably a $C_{12-22}$ fatty alcohol, and 0.5 to 30% by weight of an emulsifier, preferably 1 to 20% by weight of an anionic, nonionic, zwitterionic, or ampholytic surfactant.

Basically, the dye may be oxidatively developed with atmospheric oxygen, although it is preferred to use a chemical oxidizing agent, particularly when the hair is not only to be dyed, but also lightened in color at the same time.

Oxidation may be initiated either immediately before application of the dye preparation by mixing with an oxidizing agent or on the hair itself. In the first case, the dye preparation is mixed with an oxidizing agent, preferably with hydrogen peroxide solutions or with hydrogen peroxide adducts with urea, melamine or sodium borate, and applied to the hair after a short reaction time, the oxidation process and development of the dye then being completed during the time of action on the hair. This method of application is extremely easy and is particularly suitable for home use.

Deeper and more brilliant colors are obtained when the dye preparation is initially applied to the hair, left thereon for 10 to 30 minutes, and an oxidizing agent preparation is subsequently applied to the hair. Preferred oxidizing agents are hydrogen peroxide solutions or dispersions of potassium or ammonium peroxydisulfate or water-soluble periodates. These dispersions may be similar in composition to the carriers in the form of a cream emulsion described above for neutral or mildly acidic dye preparations. Separate application of the oxidizing agent to the hair requires more care and skill and is therefore preferably done by professional hairdressers.

After a contact time of 15 to 30 minutes, excess dye and oxidizing agent are washed out from the hair. A commercially available anionic shampoo is preferably used for this purpose. If the dye composition already has an adequate surfactant content, it is sufficient to use water.

The following Examples are intended to illustrate the invention without limiting it in any way.

EXAMPLES

1. Mildly Acidic Dyeing, Oxidation on the Hair

A dye cream emulsion of the following composition was prepared:

| | |
|---|---|
| Cetyl/stearyl alcohol (30:70) | 6 g |
| Coconut oil fatty alcohol ($C_{12-18}$) | 2 g |
| Cetyl/stearyl alcohol polyglycol ether (20 EO) | 2 g |
| 5,6-Dihydroxyindoline hydrobromide | 1 g |
| Water | 89 g |

An oxidizing agent dispersion of the following composition was prepared:

| | |
|---|---|
| Cetyl/stearyl alcohol (30:70) | 6 g |
| Coconut oil fatty alcohol ($C_{12-18}$) | 2 g |
| Cetyl/stearyl alcohol polyglycol ether (20 EO) | 2 g |
| Ammonium peroxydisulfate | 5 g |
| Water | 85 g |

The dye cream was applied to 15 cm long strands (weight about 2 g) of untreated, standardized 80% grey human hair and left to act thereon for 20 minutes at 25° C.

Without intermediate rinsing, the oxidizing agent dispersion was then applied to the same hair strands and left to act thereon for 20 minutes. The strands were then washed with a typical shampoo, rinsed with water and dried.

A mid-brown color tone and very good masking of the grey in the hair strands were obtained. Fastness to light, fastness to rubbing, and resistance to permanent-wave treatment were very good.

2. Mildly Alkaline Dyeing, Oxidation Before Application to the Hair

A dye cream emulsion of the following composition was prepared:

| | |
|---|---|
| Lauryl/myristyl alcohol (70:30) | 10 g |
| Fatty alcohol ($C_{12/14}$) ether sulfate (2EO), sodium salt, 28% solution in water | 25 g |
| Water | 60 g |
| $Na_2SO_3$ | 1 g |
| Ammonium sulfate | 1 g |
| 5,6-Dihydroxyindoline hydrobromide | 1 g |
| Concentrated ammonium solution to pH = 9.5 | |
| Water | ad 100 g |

The constituents were mixed with one another in the above order. After addition of the 5,6-dihydroxyindoline and the-ammonium sulfate (buffer), the emulsion was first adjusted to pH 9.5 with concentrated ammonia solution and was then made up with water to 100 g.

Oxidative development of the dye was carried out with 3% hydrogen peroxide solution as oxidizing agent. To this end, 50 g of hydrogen peroxide solution (3%) were added to and mixed with 100 g of the emulsion.

The dye cream was applied to about 5 cm long strands of standardized, 90% grey, but not especially pretreated human hair and left thereon for 30 minutes at 27° C. On completion of the dyeing process, the hair was rinsed, washed with a typical shampoo, and then dried.

A brilliant intensive tone in the dark brown range was obtained.

The hair color was distinguished by very good fastness properties (for example fastness to light, rubbing, cold-wave treatment and washing).

3. Use as Color Modifier Together With Known Primary Intermediate Components Hair dyes according to the invention were prepared in the form of a hair dye cream emulsion of the following composition:

| | |
|---|---|
| Fatty alcohol $C_{12-18}$ | 10 g |
| Fatty alcohol ($C_{12-14}$) ether sulfate (2 EO), sodium salt, 28% in water | 25 g |
| Water | 60 g |
| $Na_2SO_3$ | 1 g |
| $(NH_4)_2SO_4$ | 1 g |
| 5,6-Dihydroxyindoline hydrobromide | 1.74 g |
| Primary intermediate (component D) | 7.5 millimoles |
| Concentrated ammonia solution to pH 9.5 | |
| Water | ad 100 g |

Preparation of the cream emulsion, oxidative development and coloring of hair strands were carried out as described in Example 2.

The following compounds were successively used as primary intermediates (component D)

D1: p-tolylenediamine
D2: 2-chloro-p-phenylenediamine
D3: N-methyl-p-phenylenediamine
D4: N,N-diethyl-p-phenylenediamine
D5: N-(β-hydroxyethyl)-p-phenylenediamine
D6: N,N-dimethyl-p-phenylenediamine
D7: N,N-bis-(β-hydroxyethyl)-p-phenylenediamine
D8: 2,5-diaminobenzyl alcohol
D9: p-aminophenol
D10: 1-amino-4-naphthol
D11: 2,4,5,6-tetraaminopyrimidine The results of the hair dyeing tests are set out in the following Table:

| Hair dye obtained | Primary intermediate Component D | Color tone |
|---|---|---|
| 3.1 | D1 | Black |
| 3.2 | D2 | Dark violet |
| 3.3 | D3 | Black-violet |
| 3.4 | D4 | Black-blue |
| 3.5 | D5 | Black-blue |
| 3.6 | D6 | Blue-black |
| 3.7 | D7 | Blue-black |
| 3.8 | D8 | Dark violet |
| 3.9 | D9 | Dark brown |
| 3.10 | D10 | Dark brown |
| 3.11 | D11 | Brown-black |

What is claimed is:

1. A process for oxidative dyeing of keratin fibers by contacting said keratin fibers with a dyeing composition comprising a carrier and indolines, or salts of indolines, corresponding to formula I:

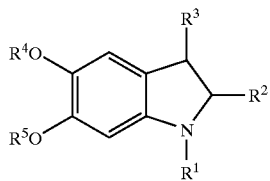

in which $R^1$, $R^2$, $R^3$, $R^4$, and $R^5$ independently of one another represent hydrogen or $C_{1-4}$ alkyl groups, or $R^4$ and $R^5$ together with the oxygen atoms to which they are attached may represent an alkylenedioxy group containing 1 to 4 carbon atoms, and causing oxidation of said dye-ing composition while it is in contact with said keratin fibers.

2. A process as claimed in claim 1, wherein, in formula I, the groups $R^1$, $R^2$, $R^3$, $R^4$, and $R^5$ are hydrogen, except that one of the groups $R^1$, $R^2$, and $R^3$ may be a methyl group.

3. A process as claimed in claim 2, wherein the indolines corresponding to formula I or salts thereof are used as color modifiers in oxidation hair dyes containing other aromatic or heterocyclic amino primary intermediate compounds.

4. Hair dyes comprising oxidation dye precursors in a carrier, wherein indolines, or salts of indolines, of formula I:

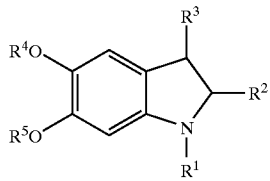

in which $R^1$, $R^2$, $R^3$, $R^4$, and $R^5$ independently of one another represent hydrogen or $C_{1-4}$ alkyl groups, or $R^4$ and $R^5$ together with the oxygen atoms to which they are attached may represent an alkylenedioxy group containing 1 to 4 carbon atoms are present in a quantity of 0.1 to 20 millimoles per 100 g of hair dye as oxidation dye precursors and the carrier is a gel containing 1 to 20% by weight of a soap or an oil-in-water emulsion containing 1 to 25% by weight of a fatty component and 0.5 to 30% by weight of an emulsifier from the group of anionic, nonionic, cationic, or ampholytic surfactants.

5. Hair dyes as claimed in claim 4, additionally comprising other aromatic or heterocyclic amino primary intermediate compounds.

6. Oxidation hair dyes as claimed in claim 5, wherein the indolines correspond to formula I when the groups $R^1$, $R^2$, $R^3$, $R^4$, and $R^5$ are hydrogen, except that one of the groups $R^1$, $R^2$, and $R^3$ may be a methyl group.

7. Oxidation hair dyes as claimed in claim 4, wherein the indolines correspond to formula I when the groups $R^1$, $R^2$, $R^3$, $R^4$, and $R^5$ are hydrogen, except that one of the groups $R^1$, $R^2$, and $R^3$ may be a methyl group.

8. A process as claimed in claim 1, wherein the indolines corresponding to formula I or salts thereof are used as color modifiers in oxidation hair dyes containing other aromatic or heterocyclic amino primary intermediate compounds.

9. A process as claimed in claim 8, wherein indolines of formula I or salts thereof are present in a quantity of 0.1 to 20 millimoles per 100 g of hair dye as oxidation dye precursors and the carrier is a gel containing 1 to 20% by weight of a soap or an oil-in-water emulsion containing 1 to 25% by weight of a fatty component and 0.5 to 30% by weight of an emulsifier from the group of anionic, nonionic, cationic, or ampholytic surfactants.

10. A process as claimed in claim 3, wherein indolines of formula I or salts thereof are present in a quantity of 0.1 to 20 millimoles per 100 g of hair dye as oxidation dye precursors and the carrier is a gel containing 1 to 20% by weight of a soap or an oil-in-water emulsion containing 1 to 25% by weight of a fatty component and 0.5 to 30% by weight of an emulsifier from the group of anionic, nonionic, cationic, or ampholytic surfactants.

11. A process as claimed in claim 2, wherein indolines of formula I or salts thereof are present in a quantity of 0.1 to 20 millimoles per 100 g of hair dye as oxidation dye precursors and the carrier is a gel containing 1 to 20% by weight of a soap or an oil-in-water emulsion containing 1 to 25% by weight of a fatty component and 0.5 to 30% by weight of an emulsifier from the group of anionic, nonionic, cationic, or ampholytic surfactants.

12. A process as claimed in claim 1, wherein indolines of formula I or salts thereof are present in a quantity of 0.1 to 20 millimoles per 100 g of hair dye as oxidation dye precursors and the carrier is a gel containing 1 to 20% by weight of a soap or an oil-in-water emulsion containing 1 to 25% by weight of a fatty component and 0.5 to 30% by weight of an emulsifier from the group of anionic, nonionic, cationic, or ampholytic surfactants.

13. A process according to claim 1, wherein the oxidation of said dyeing composition occurs with the aid of a chemical oxidizing agent selected from the group consisting of:

(i) hydrogen peroxide (ii) hydrogen peroxide adducts with urea, melamine, or sodium borate (iii) dispersions of potassium or ammonium peroxydisulfate; and (iv) periodates.

14. A process according to claim 1, wherein the chemical oxidizing agent consists of water soluble periodates.

* * * * *